United States Patent
Gou et al.

(10) Patent No.: US 8,323,583 B2
(45) Date of Patent: Dec. 4, 2012

(54) DETECTION DEVICE

(75) Inventors: Lijian Gou, Hangzhou (CN); Haipeng Hu, Hangzhou (CN)

(73) Assignee: Alere Switzerland GmbH, Zug (CH)

( * ) Notice: Subject to any disclaimer, the term of this patent is extended or adjusted under 35 U.S.C. 154(b) by 0 days.

(21) Appl. No.: 13/143,068

(22) PCT Filed: Jan. 5, 2010

(86) PCT No.: PCT/CN2010/000015
§ 371 (c)(1),
(2), (4) Date: Aug. 1, 2011

(87) PCT Pub. No.: WO2010/075814
PCT Pub. Date: Jul. 8, 2010

(65) Prior Publication Data
US 2011/0281344 A1    Nov. 17, 2011

(30) Foreign Application Priority Data
Jan. 5, 2009    (CN) .......................... 2009 1 0095233

(51) Int. Cl.
*G01N 1/02* (2006.01)
*G01N 31/22* (2006.01)

(52) U.S. Cl. ......... 422/402; 422/430; 422/557; 422/559

(58) Field of Classification Search .................. 422/402, 422/430, 557, 559
See application file for complete search history.

(56) References Cited

U.S. PATENT DOCUMENTS

| | | | | |
|---|---|---|---|---|
| 5,595,187 A * | 1/1997 | Davis | ............................ | 600/584 |
| 6,074,606 A * | 6/2000 | Sayles | ............................ | 422/417 |
| 6,095,886 A * | 8/2000 | Beckman et al. | ............ | 446/267 |
| 6,168,758 B1 * | 1/2001 | Forsberg et al. | .............. | 422/412 |
| 6,375,897 B1 * | 4/2002 | Bachand | ....................... | 422/401 |
| 6,726,879 B2 * | 4/2004 | Ng et al. | ........................ | 422/417 |
| 7,300,626 B2 * | 11/2007 | Wu et al. | ....................... | 422/404 |
| 7,458,942 B2 | 12/2008 | Bohannon et al. | | |
| 2002/0046614 A1 * | 4/2002 | Alley | .......................... | 73/864.91 |
| 2005/0106750 A1 * | 5/2005 | Tung et al. | .................... | 436/169 |
| 2006/0064032 A1 * | 3/2006 | Bohannon et al. | ........... | 600/573 |
| 2006/0280650 A1 * | 12/2006 | Wong et al. | .................... | 422/58 |

FOREIGN PATENT DOCUMENTS

| | | |
|---|---|---|
| CN | 201156047 | 11/2008 |
| CN | 101556277 | 10/2009 |
| CN | 201335837 | 10/2009 |

* cited by examiner

*Primary Examiner* — Jill Warden
*Assistant Examiner* — Brittany Fisher
(74) *Attorney, Agent, or Firm* — DLA Piper LLP (US)

(57) ABSTRACT

A detection device and a detection method are disclosed. The detection device comprises a sample inlet (132) that allows liquid samples flowing from a collection chamber (20) to a detection chamber (10), which comprises a through hole (135) that allows gases circulation between the detection chamber and the collection chamber, and a sheath (140) that prevents liquid samples from entering into the detection chamber from the collection chamber via the through hole. The detection chamber contains test reagent strips (120) to detect whether samples contain interested analytes. The detection device further comprises a protrusion (131) that enables the detection device standing tilted in the traverse direction. The detection method comprises collecting liquid samples as the first step, followed by standing the device tilted in its traverse direction through a protrusion support, and detecting whether samples contain the analytes.

18 Claims, 8 Drawing Sheets

DETECTION DEVICE

CROSS REFERENCE TO RELATED APPLICATIONS

This application is a 35 USC §371 National Stage application of International Application No. PCT/CN2010/000015 filed Jan. 5, 2010, now pending; which claims the benefit under 35 USC §119(a) to China Patent Application Serial No. 200910095233.3 filed Jan. 5, 2009. The disclosure of each of the prior applications is considered part of and is incorporated by reference in the disclosure of this application.

TECHNICAL FIELD

The present invention relates to a detection device, in particular a detection device for detecting liquid samples of illegal drugs.

BACKGROUND ART

Illegal drugs have become more and more easily accessible to ordinary people and their use more and more popular. In order to ensure safe working environments and fair competitions in sports, enterprises, companies and sport organizations often need to test body fluids such as urine of employees and athletes to find out whether they have used illegal drugs. Consequently, more and more devices for collecting and detecting samples of body fluids are available, particularly those designed for the use of non-professionals at ordinary situations. Traditional devices for collecting and detecting samples of body fluids, however, cannot detect samples as safe and accurate as desired due to problems such as sample leakage and inaccurate amount of sample, the latter may lead to flooding or failure of detection.

U.S. Pat. No. 5,119,830 discloses such a device, wherein the detection device is disposed on a lid of a urine cup. When the lid is open, the cup can be used to collect and store liquid samples. When detection is needed, sample is first collected, then a protrusion part on the lid is pressed to break a septum between the detection device and the cup, and then the cup is reversed for a period of time to allow the sample entering into a water absorbing part of the detection device from the cup along the gap broken by the protrusion so that the detection can be carried out.

U.S. Pat. No. 5,595,187 discloses another similar detection device, wherein the detection device is also disposed on a lid. When liquid sample is collected and is ready for detection, a valve on the lid is pressed to allow entering of the sample into a cavity temporarily; after a period of time, the valve is released and the cup is reversed, thus contacting the liquid sample in the cavity with the detection device for a detection reaction.

US Patent Application No. 2004/0081581 also discloses a detection device, wherein fluid is introduced to a test reagent strip by using filter paper. By reversing the cup, the device allows liquid sample to contact with a filter paper pad, through which the sample is further guided to contact a water absorbing part of the test strips. Such a device normally does not have the problem of having excess amount of sample, but it may fail in detection because of insufficient amount of sample.

In addition, U.S. Pat. No. 6,726,879 B2 discloses a urine cup for detection in standing titled in the traverse direction. The urine cup includes a collection chamber, a liquid transferring chamber, a detection chamber, and two cup lids; wherein one cup lid is for sealing the collection chamber and another for detecting whether the sample contains analytes. The patented invention achieves the purpose of detection by directly contacting the sample receiving area at the upstream region of a test reagent strip with the liquid sample.

SUMMARY OF THE INVENTION

The present invention provides a detection device, which comprises a sample inlet allowing passing of liquid from a collection chamber to a detection chamber, the detection chamber further comprises a through hole enabling circulating of gas between the detection chamber and the collection chamber, and a sheath for preventing liquid from entering into the detection chamber from the collection chamber via the through hole.

Preferably, the through hole is positioned higher than where the sample inlet is positioned. More preferably, the through hole allows gas but not liquid passing through.

In a specific embodiment, the detection device comprises a cup lid, the detection chamber is disposed inside the cup lid and the sheath is at the back of the cup lid. The sheath is tubular and comprises an opening for allowing circulation of gas between the sheath and the collection chamber. Preferably, the opening is located at a position higher than that of the through hole. Further preferably, edge of the sheath is sealingly connected with the cup lid.

In another preferably embodiment, the through hole allows liquid passing through. The sheath has an opening end located at a position higher than that of the through hole.

Further preferably, the through hole is located at a position lower than that of the sample inlet. The through hole allows gas but not liquid in and out. The sheath has an opening end located at a position higher than that of the through hole.

In the above preferred embodiments, the detection device further comprises a protrusion enabling the detection device standing titled in the traverse direction.

The present invention also relates to a detection device comprising a cup lid having a detection chamber, wherein the cup lid comprises a sample inlet that allows passing of liquid from the collection chamber into the detection chamber, a through hole that enables circulating of gas between the detection chamber and the collection chamber, and a sheath that prevents the liquid from entering into the detection chamber from the collection chamber via the through hole. Preferably, the through hole is located at a position higher than that of the sample inlet. More preferably, the through hole allows gas but not liquid in and out. The sheath comprises an opening for allowing circulation of gas between the sheath and the collection chamber.

The present invention further relates to a detection device comprising a cup lid having a detection chamber and a cup body having a collection chamber; the cup lid comprises a sample inlet that allows passing of liquid from the collection chamber into the detection chamber. The cup lid further comprises a through hole enabling circulating of gas between the detection chamber and the collection chamber, and a sheath for preventing the liquid from entering into the detection chamber from the collection chamber via the through hole. Preferably, the through hole is located at a position higher than that of the sample inlet. More preferably, the sheath comprises an opening for allowing circulation of gas between the sheath and the collection chamber. More preferably, the detection device further comprises a protrusion on the cup lid for supporting the detection device standing titled in the traverse direction.

The preset invention further relates to a detection device comprising a cup lid having a detection chamber and a test reagent strip, and a cup body having a collection chamber; the cup lid comprises a sample inlet that allows liquid passing from the collection chamber into the detection chamber; wherein the cup lid further comprises a through hole enabling circulation of gas between the detection chamber and the collection chamber, and a sheath for preventing the liquid from entering into the detection chamber from the collection chamber via the through hole. Preferably, the through hole is located at a position higher than that of the sample inlet; and the sheath comprises an opening for allowing circulation of gas between the sheath and the collection chamber.

The present invention has the benefits including: carrying out accurate detection by maintaining quantified liquid sample in the detection chamber through using the through hole and the sheath during the absorption of the liquid sample, and keeping circulation of gas in the cup lid and smooth flowing of the liquid sample within the detection chamber by allowing gas therein moving freely.

Figure 1:
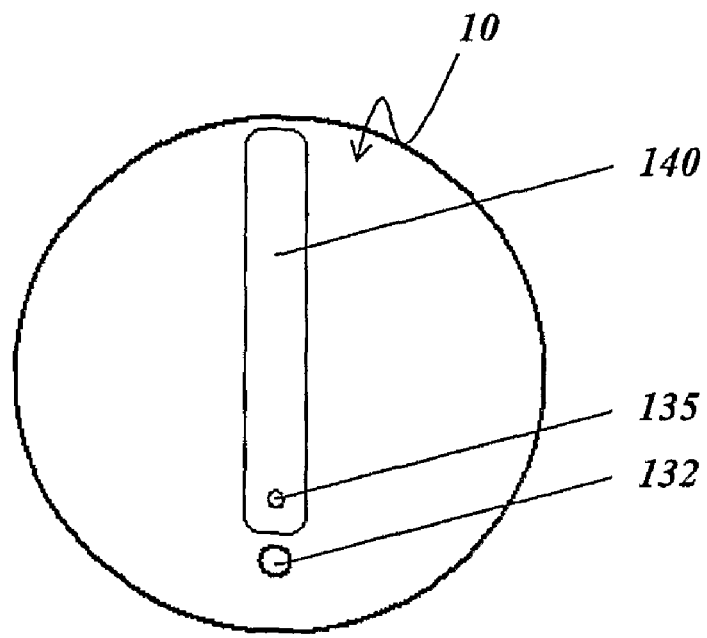
FIG. 1 is a sketch diagram of an example of the present invention.

Explanation of the reference signs: urine cup 1, cup lid 10, upper lid 110, reagent strip 120, carrier 130, protrusion 131, sample inlet 132, grid 133, screw thread of cup lid 134, through hole 135, clip trough 136, cavity 137, sheath 140, seal ring 150; cup body 20, screw thread of cup body 210

DESCRIPTION OF THE PREFERRED EMBODIMENTS OF THE INVENTION

The structure or the used technical phrases of the present invention are further illustrated here below.

Detection

As used here, "detection" means testing or assaying the existence of a substance or a material, such as but not limited to, a chemical substance, an organic compound, an inorganic compound, a metabolic product, a drugs or a drug metabolite, an organic tissue or a metabolite of organic tissues, nucleic acid, protein or polymer; in addition, it also means testing and assaying the content of a substance or material. Further, assay used here includes immune assay, chemical assay, enzymatic assay and the like.

Samples

Samples of the present invention refer to substances that can be used to test, assay or diagnose whether they contain interested analytes. Samples can be, for example, liquid samples including blood, blood plasma, blood serum, urine, saliva and various secretory fluids, and solutions formed by pre-treating solid samples and semi-solid samples. The collected samples can be used for immune assay, chemical assay, enzymatic assay and the like to determine whether they contain analytes.

Analytes

The device and method of the present invention can be used to analyze any analytes. The analytes can be detected in any liquid or liquid samples such as urine, saliva, slobber, blood, blood plasma or blood serum.

The analytes can further be some semi-antigen substances including the drugs (such as the abused-used drugs). "Drugs of abuse" refers to drugs taken not for medicinal purpose (typically serves for paralysis of nerves). The device of the present invention can also be use to detect drugs administrated for medicinal purpose but could be easily taken excessively. These drugs include tricyclic antidepressants (imipramine or analogs), acetaminophenol and the like. Such drugs will be decomposed into different small molecular materials after absorbed by human body, and these small molecular materials present in body fluids such as blood, urine, saliva, sweat or portions of these body fluids.

Detection Device

Figure 5:
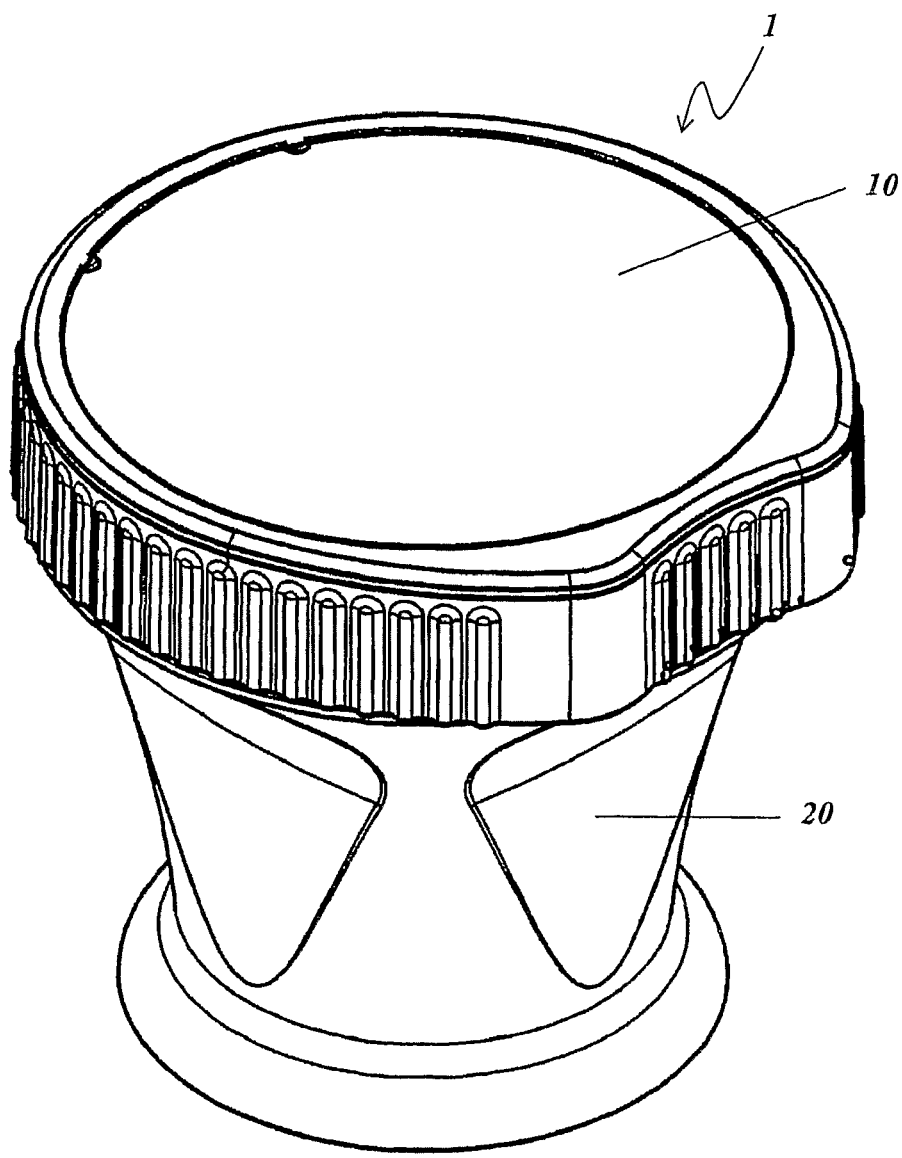
FIG. 5 is a stereogram of an example of the present invention.
Figure 6:
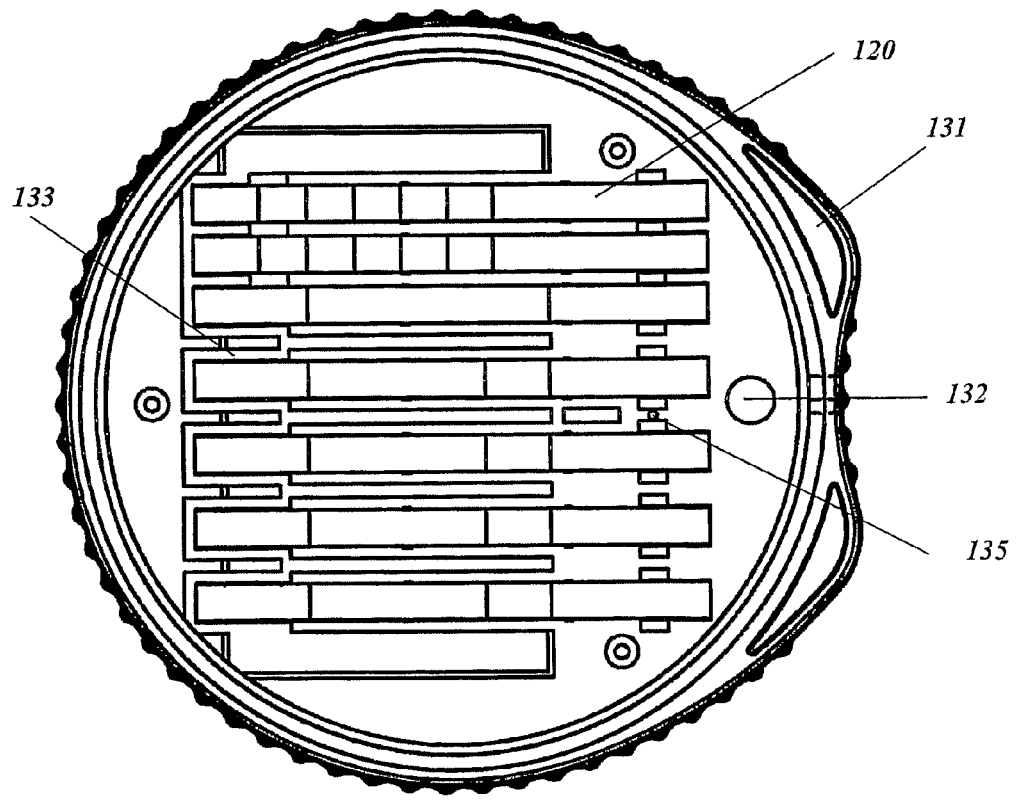
FIG. 6 is a front view of the cup lid of the present invention.
Figure 7:
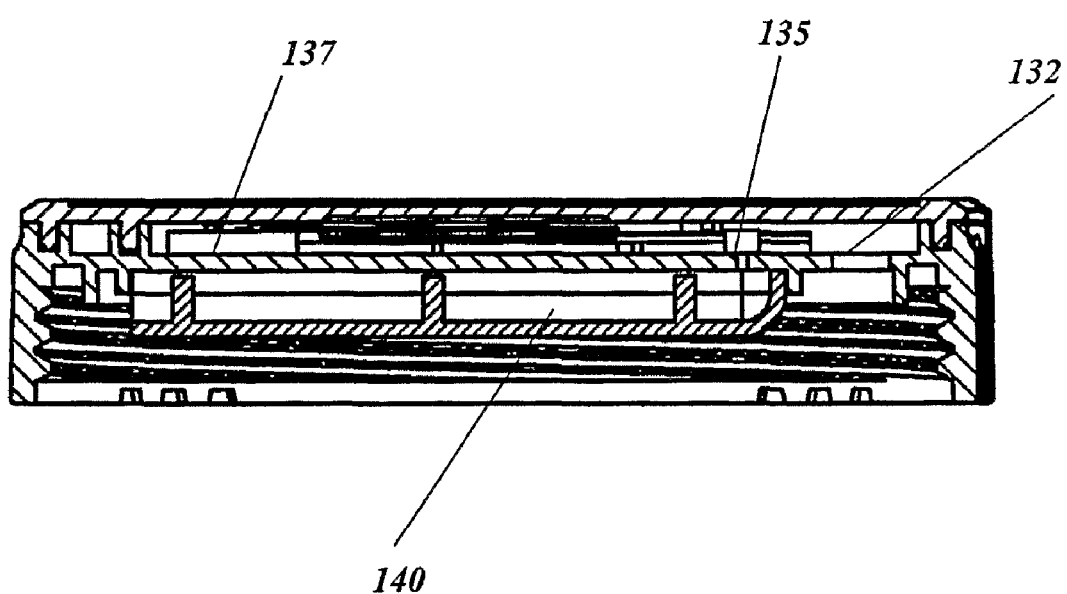
FIG. 7 is a side sectional view of the cup lid of the present invention.
Figure 8:
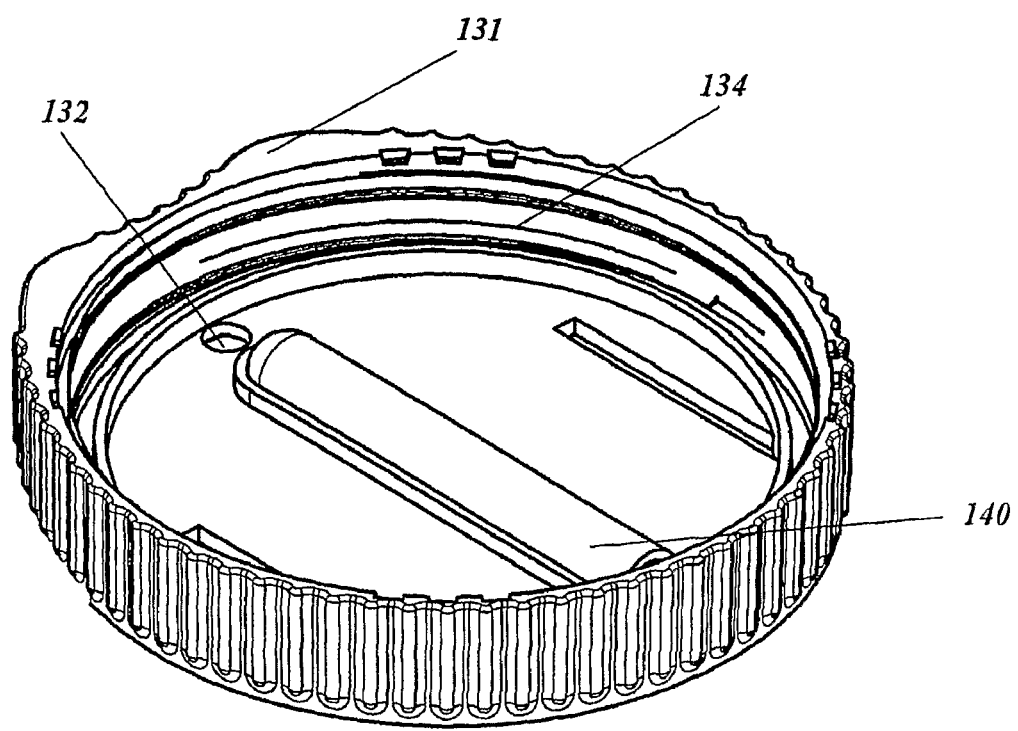
FIG. 8 is a stereogram of the back of the cup lid.

The detection device is a device used to analyze whether samples contain analytes, and preferably, is a device to collect liquid samples such as urine and to analyze the analytes contained therein (such as drugs and metabolic products thereof). The detection device can be a detection chamber 10, in particular a cup lid 10, and can also be a urine cup 1 comprising a detection chamber and a collection chamber. More preferably, the urine cup 1 can be made of various materials, such as plastics of various specifications, and have different shapes. As shown in FIG. 5, the urine cup 1 can consist of the cup lid 10 and the cup body 20.

Figure 2:
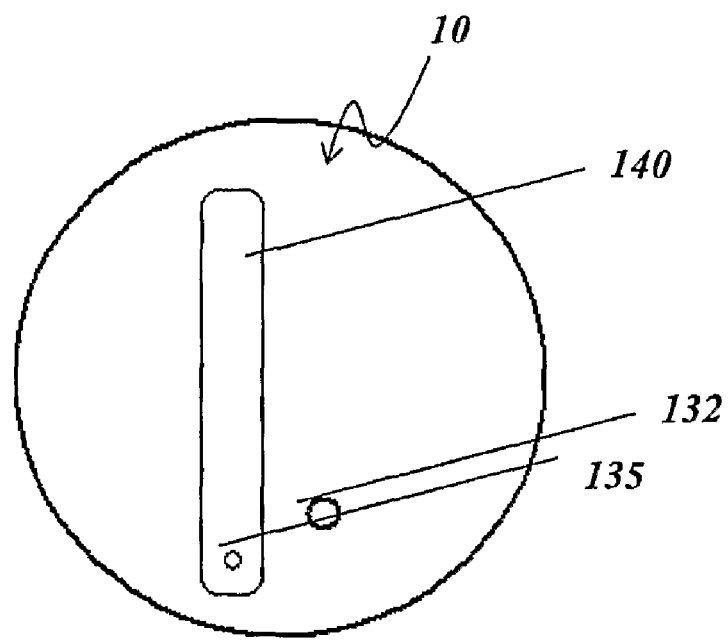
FIG. 2 is a sketch diagram of another example of the present invention.

The cup lid 10 can include a cavity 137 for containing liquid. The cavity 137 can have a sample inlet 132 that allows passing through of liquid from the collection chamber to the detection chamber, and a gas exchange hole or a through hole 135 that allows circulation of gas between the detection chamber and the collection chamber. The surrounding of the cavity 137 is sealed by a seal ring 150, and the sample inlet 132 is the only in/out channel of liquid from the collection chamber to the detection chamber. Except for the sample inlet 132 and the through hole 135, which are in/out passages of liquid and/or gas, the other parts of the cavity 137 are all sealed against gas and liquid. The cavity 137 consists of the carrier 130 and the upper lid 110, and the reagent strip 120 is fixed on the carrier 130. As shown in FIG. 2, the cavity 137 contains the reagent strip 120 for detecting whether samples contain interested analytes. The reagent strip 120 can be one strip or a set of strips. Strips similar to the reagent strip 120 have been clearly illustrated in prior art and are not repeatedly described herein.

The cup lid 10 can further include the sample inlet 132 that allows liquid sample to enter into the cavity 137, and the sample inlet 132 is covered with one or several layers of water absorbing material such that the liquid sample can be absorbed directly or indirectly. The material can be filter paper, glass fiber, pledget, nitrocellulose membrane or all other materials that can contain and transfer water or other liquids. Preferably, the sample inlet 132 is covered with filer paper. Transferring liquid sample through filter paper may slow down the speed of the flowing of liquid sample from the cup body 20 to the reagent strip 120 and can avoid "flooding" resulted from flowing too fast. More preferably, water absorbing pad covered on the sample inlet 132 is composed of fiber glass and filter paper. The filter paper is good at water absorbing and fiber glass is good at liquid transferring. The combination of the both can better transfer the liquid sample. More preferably, the water absorbing pad consists of three layers, including a thick layer of filer paper, a layer of glass fiber and a thin layer of filter paper, with the thin filter paper at the bottom, glass fiber in the meddle and the thick filter paper at the top. The thin filter paper allows liquid to pass through easily while the thick filter paper blocks excessive amount of liquid. In another more preferably embodiment, the sample inlet 132 can be a simple opening, which facilitates passing through of liquid directly. This arrangement makes liquid sample flow more fluently.

Figure 3:
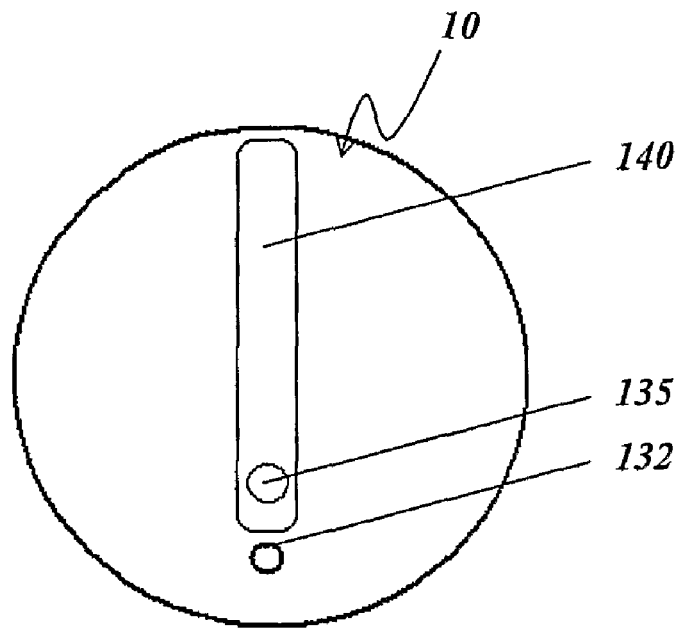
FIG. 3 is a sketch diagram of another example of the present invention.
Figure 4:
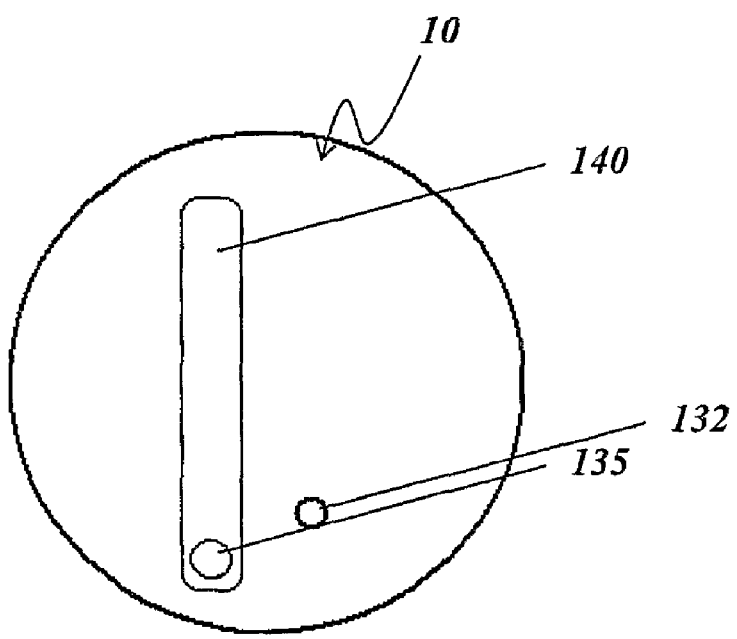
FIG. 4 is a sketch diagram of another example of the present invention.

There may be a through hole 135 for allowing circulation of gas between the detection chamber and the collection chamber in the cup lid 10. The through hole 135 can be on any position of the detection device. Preferably, as shown in FIGS. 1 and 3, the through hole 135 is located at a position higher than that of the sample inlet 132. The meaning of higher than the position of the sample inlet 132 refers to that when flowing in the detection device, the level of liquid sample reaches the position of the through hole 135 after submerging the sample inlet 132 or in other word, after the sample inlet 132 is blocked out by the liquid sample when the sample enters into the detection chamber from the sample inlet 132. This arrangement of positions is referred to as that the through hole 135 is located at a position higher than that of the sample inlet 132. Likewise, as shown in FIGS. 2 and 4, the through hole 135 is located at a position lower than that of the sample inlet 132 refers to that when flowing, the liquid sample enters into the detection chamber from the sample inlet firstly, and when the through hole 135 has been in contact with the sample and is blocked out by the sample, the sample inlet 132 still allows passing of liquid between the detection chamber and the collection chamber. This arrangement of positions is referred to as that the through hole 135 is located at a position lower than that of the sample inlet 132. In specific embodiments, the size of the through hole 135 can be as shown in FIGS. 1 and 2. The through hole can be called a gas hole since it only allows gas but not liquid in and out. There can be one, two, three or more such through hole 135. The through hole 135 can be located anywhere on the cup lid 10, and can be preferably, as shown in FIG. 5, adjacent to the sample inlet 132 for allowing in and out of liquid. Further preferably, the through hole 135 can be protected by the sheath 140 that is used to prevent liquid from entering into the detection chamber from the collection chamber via the through hole 135. The through hole 135 acts to ensure gas circulation in the cup body 20 and the cup lid 10 during transferring of liquid sample. If without the through hole 135, when the cup body 20 is overturned 90 degree, which is a very short time span, samples will quickly cover the sample inlet and form a liquid sealing surface across the sample inlet 132 and consequently inhibits remaining samples from entering into the cup lid 10. In this case, the detection will fail due to insufficient amount of samples. By having the through hole 135, air in the cup lid 10 can be push out through the through hole 135 when samples enter into the sample inlet 132, thereby preventing to form a liquid surface that blocks the sample inlet 132. More preferably, the through hole 135 is located adjacent to the sample inlet 132 and the water absorbing pad, which facilitates gas circulating and exchanging. More preferably, the through hole 135 is located adjacent to the sample absorbing area of the reagent strip 120. To arrange the through hole 135 in this manner helps the water absorbing pad fully absorb liquid samples. More preferably, the through hole 135 is covered with a filter paper strip.

In specific embodiments, when the through hole 135 is at a position higher than that of the sample inlet 132, liquid sample in the collection chamber enters into the detection chamber via the sample inlet 132 firstly, then air in the detection chamber is discharged to the sheath via the through hole 135 and is kept circulating with the air in the collection chamber. Finally, the sample surface in the detection chamber reaches the position of the through hole 135, because except for the through hole 135 and sample inlet 132, all other parts of the detection chamber are sealed, the gas exchange among the detection chamber, the sheath and the collection chamber stops and the sample surface stops rising once the liquid sample flood over the through hole 135. At this time, the sample cannot enter the sheath via the through hole, and the detection chamber thus contains certain amount of sample. In particular, because of the existence of the through hole 135, the height of the liquid sample in cavity 137 is limited. When liquid sample enters into the cavity via the sample inlet 132, its surface will continuously rise until it inundate the through hole 135, when the sample stops entering into the cavity 137. Thus, the position of the through hole 135 determines the height or the surface level of the sample in the cavity 137. Further preferable, through adjusting the size of the cavity 137 and the distance between the through hole 135 and the surrounding edge of the cavity 137, volume of the sample allowed to entered into the cavity 137 can be quantified. In another specific embodiment, the through hole 135 is positioned lower than that of the sample inlet 132, which can better quantify the sample since the liquid sample will substantially stop entering into the detecting chamber from the sample inlet 132 after arriving at the level of the through hole 135.

The through hole 135 can be used to allow liquid passing through, as shown in FIGS. 2 and 4. When the through hole 135 is located at a position higher than that of the sample inlet 132, the liquid sample can enter into the detection chamber from the collection chamber via the sample inlet 132. During this process, the through hole 135 keeps discharging gas, liquid sample in the detection chamber reaches the position of the through hole 135 and then enters the sheath 140. Finally, the level of the sample surface in the sheath 140 is consistent with that in the collection chamber, and the level of the sample surface in the detection chamber is kept above the through hole 135, thus quantifying the sample in the detection chamber. In another specific embodiment, when the position of the through hole 135 is lower than that of the sample inlet 132, the liquid sample also enters into the detection chamber via the sample inlet 132 firstly; when the sample level in the detection chamber arrives at the position of the through hole 135, the fed speed of the sample is slowed or the sample substantially stops entering into the detection chamber, thus achieving a relatively better quantifying result.

Figure 9:
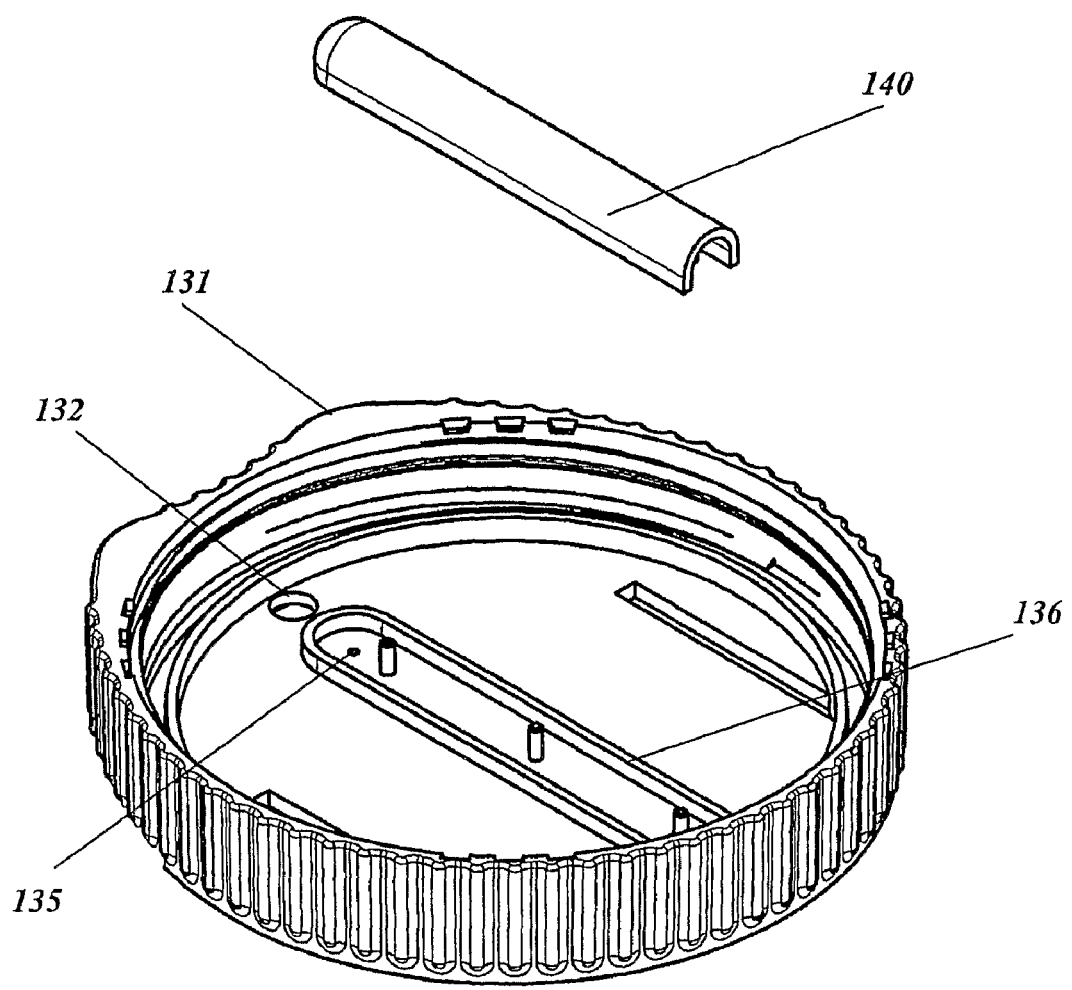
FIG. 9 is a stereo-exploded view of the back of the cup lid.
Figure 10:
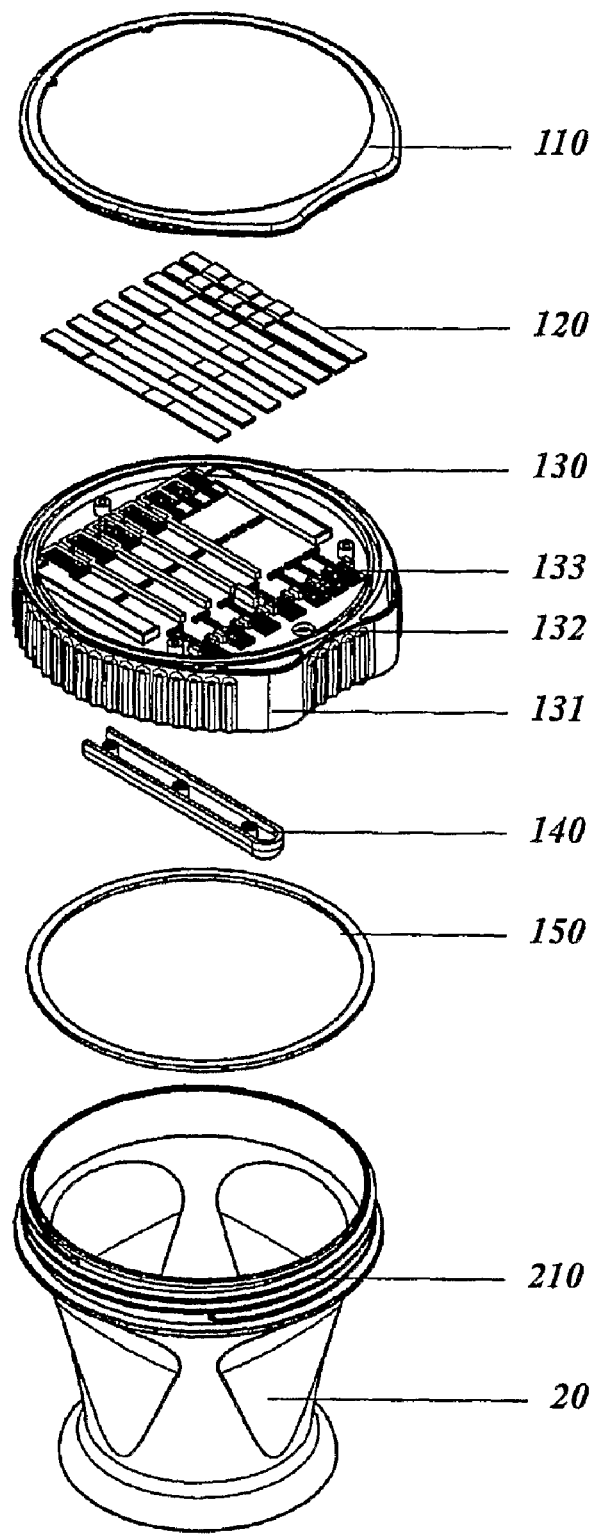
FIG. 10 is a stereo-exploded view of the urine cup of the present invention.

The cup lid 10 further includes the sheath 140 (as shown in FIG. 9), which is for preventing liquid from entering the detection chamber from the collection chamber via the through hole 135. This sheath 140 may be disposed on the backside of the cup lid 10. Herein the backside of the cup lid refers to the side of the cup lid facing the collection chamber, or the side away from the detection chamber. When the urine cup 1 is overturned sideways, since the amount of liquid sample in the cup body 20 is not easily controlled and its surface level can easily goes beyond the position of the through hole 135 on the cup lid, thus the through hole 135 will be blocked and the gas cannot be further discharged. To have a sheath 140 can protect the through hole 135 from being flooded over by the liquid sample. The sheath of the through hole 135 can have many forms. Preferably, the sheath 140 can be an element having one end open and another end closed with the through hole 135 being covered within the closed end. The opening end is preferably at a position far away from the through hole 135. The sheath 140 in this form can protect the through hole 135 from being affected such that the through hole can still discharge gas even when the cup body 20 contains comparatively large amount of sample. Further preferably, the sheath 140 can have two or more than two openings, which will not affect the performance of the sheath 140. Further preferably, the sheath 140 can protect one through hole 135 or more through holes 135. The sheath 140 can be cylindrical, tubular or other shapes that can easily cover the through hole 135 and keep it ventilating. Preferably, the sheath 140 is tubular. In this shape, the sheath 140 includes an end closer to the through hole 135 that is closed and another end away from the through hole 135 that is open. The sheath 140 can be positioned in different ways on the cup lid 10. Preferably, the distance between the opening of the sheath 140 and the through hole 135 is larger than the distance between the closed end of the sheath 140 and the through hole 135. More preferably, the distance between the through hole 135 and the sample inlet 132 is greater than the distance between the sample inlet 132 and the closed end of the sheath 140. It is to say that, along the flowing direction of the sample during detection, from the upstream to the downstream, the suitable sequence is the sample inlet 132, the closed end of the sheath 140, the through hole 135 and the opening of the sheath 140. More preferably, these elements traverse the central line of the cup lid 10 and are positioned on the central line. More preferably, the sample inlet 132, the closed end of the sheath 140 and the through hole 135 are at one half of the central line; and the opening of the sheath 140 is at another half of the central line. The sheath 140 can be connected with the cup lid 10 by various ways. Preferably, the sheath 140 and the cup lid 10 are connected sealingly so that the liquid sample does not flow into the sheath 140 along the edge of the sheath 140 to cause the result of sealing the through hole 135. The sealed connection can be rivet connection, clip connection, welding connection, adhesive connection and the like. As shown in FIGS. 4 and 5, the tubular sheath 140 is connected with the cup lid 10 via the clip trough 136 on the bottom of the cup lid 10, the sheath 140 and the clip trough 136 can be connected by welding to effectively ensure that no leakage will occur at the edge of the tubular sheath 140 when contacting with the liquid sample.

The cup lid 10 further includes a protrusion 131 that enables the urine cup 1 standing titled in the traverse direction, where the major axis of the cup is substantially parallel to the horizontal support surface. Since the cup lid 10 is typically rounded or has a form that can be easily roll, the protrusion 131 is used to keep the urine cup 1 stable when it stands titled in the traverse direction, which will prevent the liquid sample from entering the sheath 140 to seal the through hole 135 and consequently inhibiting discharge of gas. It can have one, two or even more protrusion 131. The protrusion 131 can be located at the end closer to the sample inlet 132 and the through hole 135. Preferably, the distance between the protrusion 131 and the sample inlet 132 is shorter than the distance between the protrusion 131 and the through hole 135. While enabling the urine cup 1 standing titled in the traverse direction, the protrusion 131 also allows the test reagent strip 120 in the cup lid 10 in a substantially vertical orientation, which is an optimal orientation for the reagent strip to test the liquid sample. Preferably, it can have two protrusions 131 symmetrically disposed at each side of the sample inlet 132.

In order to detect a liquid sample, the liquid sample needs to be collected first, then the cup lid 10 is tightly screwed on the cup body 20. Matching the cup lid 10 with the cup body can be achieved through tightly engaging screw thread 134 of the cup lid with screw thread 210 of the cup body. Then when the urine cup 1 stands sideward in a traverse direction, the liquid sample in the cup body 20 can reach the sample receiving area of the reagent strip 120 in the cup lid 10 via the sample inlet 132. Since the test reagent strip 120 and the sample inlet 132 are in vertical orientation, the sample inlet 132 can allow the liquid sample in the cup body 20 enter into the detection chamber horizontally, while the gas in the cup lid 10 can be discharged easily at the same time due to the protection of the sheath 140. When the surface level of the liquid sample in the cup lid 10 rises to the position of the through hole 135, naturally the hole 135 is sealed by the liquid and gas exchange between in and out of the cup lid 10 stops. This arrangement can be used to carry out quantified detection by setting up the position of the through hole 135 and the size of the cup lid 10, wherein the volume of the sample to be tested can be maintained at a constant level.

The cup lid 10 also includes a positioning device. The positioning can be carried out through screw and bolt, or through clip trough 136 and protrusion 131. The positioning device can precisely assemble the upper lid 110 and the carrier 130 during the assembling without causing problems such as declining of the carrier 130. The manner of screw and bolt are used preferably, which includes providing at least two screws on the upper lid 110 and bolts of corresponding size on the corresponding positions of the carrier 130. When assembling, it only needs to aim the screws at the bolts and then the carrier 130 is positioned on the upper lid 110 accurately.

The cup lid 10 further includes a seal ring 150 used to improve the sealing property of the interface between the cup lid 10 and the cup body 20 such that the liquid sample cannot be leaked out easily from the cup body 20. The seal ring 150 can be a "O" ring and can also be in other shapes. The seal ring 150 can be made of rubber, preferably silicon rubber. A seal ring made of silicon rubber has better sealing property and cannot be deformed easily. Preferably, it uses a seal ring 150 in the interface between the upper lid 110 and the carrier 130 and another seal ring 150 in the interface between the carrier 130 and the cup body 20, which can better prevent the liquid sample from leaking.

The embodiments of the prevent invention are illustrated in detail through the following specific figures. These specific embodiments are only limited examples without departing from the spirits of the present invention. They do not exclude other specific embodiments obtained by those skilled in the art from the combination of the existing technology and the present invention.

EXAMPLES

Example 1

As shown in FIGS. 5 to 10, the urine cup 1 includes the cup lid 10 and the cup body 20. The cup lid 10 includes the upper lid 10, the reagent strip 120, the carrier 130, the sheath 140, the seal ring 150 and two protrusions 131 for supporting the urine cup 1 standing titled in the traverse direction. The carrier 130 is provided with the test reagent strip 120, the strip-shaped grid 133, the through hole 135 and the sample inlet 132 for allowing entry of the liquid sample. The back of the carrier 130 is provided with the tubular sheath 140 welded through the clip trough 136 on the back of the carrier 130 to achieve the state of sealing. The sample inlet 132 is located at periphery of the carrier 130 and has a rectangular opening. Above the sample inlet is provided with a through hole 135. These elements are arranged, along the direction of the liquid sample flowing during detection, in the sequence of first the protrusion 131, then the sample inlet 132, then the closed end of the sheath 140, then the through hole 135 and finally the opening end of the sheath 140. Assembled cup lid 10 is all sealed except for the sample inlet 132 and the through hole 135, which connect to the outside and allow passing through of gas or liquid. This is to ensure that, during the detection process, sample will not leak out to cause contamination, and there will be no such situation that the through hole 135 cannot control the surface level of the sample in the detection chamber due to air leakage. To conduct the detection process, sufficient amount of the liquid sample needs to be collected in the cup body 20 and then the urine cup 1 is stood tilted in the traverse direction, the sample consequently enters into the cavity 137 of the cup lid via the sample inlet 132. The liquid flows fluently when the surface level of the sample has not reached the position of the through hole 135. That is because that at the backside of the cup lid 10, the through hole 135 is protected by the sheath 140 and cannot be submerged under and sealed by the liquid sample in the collection chamber; and at the detection chamber side of the cup lid 10, the liquid sample has not risen to the position of the through hole 135 and the through hole 135 still can discharge gas successfully. When the liquid sample arrives at the through hole 135 along the water absorbing pad, the through hole 135 is blocked and the air in the cup lid 10 and the cup body 20 cannot circulate and exchange. At this time the cavity 137 has sufficient amount of sample for the use of the reagent strip 120 for analyte detecting. The sample moves along the sample collection region and arrives at the detection region of the reagent strip 120 and is finally determined whether contains interested analytes. The cup lid 10 further includes four positioning nails and positioning pins positioned in the center of the cup lid 10. These positioning elements make the assembling convenient and can precisely coordinate the carrier 130 and the upper lid 110.

The invention claimed is:

1. A detection device, comprising a sample inlet that allows passing of liquid from a collection chamber to a detection chamber, wherein the detection chamber further comprises a through hole enabling circulation of gas between the detection chamber and the collection chamber, and a sheath for preventing liquid from entering into the detection chamber from the collection chamber via the through hole;
wherein the detection device comprises a cup lid, and the detection chamber is within the cup lid, while the sheath is on the underside of the cup lid covering the through hole; and
wherein the sheath is tubular.

2. A detection device according to claim 1, wherein the through hole is positioned higher than where the sample inlet is positioned.

3. A detection device according to claim 2, wherein the through hole allows passing through of gas but not liquid.

4. A detection device according to claim 1, wherein the sheath comprises an opening for allowing circulation of gas in the sheath and the collection chamber.

5. A detection device according to claim 4, wherein the sheath has an opening located at a position higher than that of the through hole.

6. A detection device according to claim 2, wherein the through hole allows liquid passing through.

7. A detection device according to claim 6, wherein the sheath has an opening end located at a position higher than that of the through hole.

8. A detection device according to claim 1, wherein the through hole is located at a position lower than that of the sample inlet.

9. A detection device according to claim 8, wherein the through hole allows passing through of gas but not liquid.

10. A detection device according to claim 9, wherein the sheath has an opening end located at a position higher than that of the through hole.

11. A detection device according to claim 1, wherein the detection device further comprises a protrusion enabling the detection device standing tilted in the traverse direction.

12. A detection device according to claim 2, wherein the detection device further comprises a protrusion enabling the detection device standing tilted in the traverse direction.

13. A detection device, comprising a cup lid having a detection chamber, the cup lid comprises a sample inlet that allows passing of liquid from the collection chamber into the detection chamber, wherein the cup lid further comprises a through hole enabling circulation of gas between the detection chamber and the collection chamber, a sheath on the underside of the cup lid covering the through hole for preventing the liquid from entering into the detection chamber from the collection chamber via the through hole; and wherein the edge of the sheath is sealindy connected with the cup lid.

14. A detection device according to claim 13, wherein the through hole is located at a position higher than that of the sample inlet.

15. A detection device according to claim 14, wherein the through hole allows passing through of gas but not liquid.

16. A detection device according to claim 15, wherein the sheath comprises an opening for allowing circulation of gas in the sheath and the collection chamber.

17. A detection device, comprising a cup lid having a detection chamber and a test reagent strip, and a cup body having a collection chamber, wherein the cup lid comprises a sample inlet that allows passing of liquid from the collection chamber into the detection chamber, and further comprises a through hole enabling circulation of gas between the detection chamber and the collection chamber, and a sheath on the underside of the cup lid covering the through hole for preventing the liquid from entering into the detection chamber from the collection chamber via the through hole.

18. A detection device according to claim 17, wherein the through hole is located at a position higher than that of the sample inlet, and the sheath comprises an opening for allowing circulation of gas in the sheath and the collection chamber.

* * * * *